(12) United States Patent
Peckham et al.

(10) Patent No.: US 9,017,395 B2
(45) Date of Patent: Apr. 28, 2015

(54) VASCULAR PROSTHESIS AND METHODS OF USE

(75) Inventors: John Peckham, St. Louis, MO (US); Mary Ann Parker, legal representative, St. Louis, MO (US); Michael Hogendijk, Mountain View, CA (US); Gerald Ray Martin, Redwood City, CA (US); Eric W. Leopold, Redwood City, CA (US)

(73) Assignee: Novostent Corporation, Mountain View, CA (US)

( * ) Notice: Subject to any disclaimer, the term of this patent is extended or adjusted under 35 U.S.C. 154(b) by 912 days.

(21) Appl. No.: 11/716,521

(22) Filed: Mar. 9, 2007

(65) Prior Publication Data

US 2008/0221665 A1    Sep. 11, 2008

(51) Int. Cl.
*A61F 2/88* (2006.01)
*A61F 2/91* (2013.01)
*A61F 2/82* (2013.01)

(52) U.S. Cl.
CPC . *A61F 2/885* (2013.01); *A61F 2/88* (2013.01); *A61F 2/91* (2013.01); *A61F 2002/823* (2013.01); *A61F 2220/0058* (2013.01)

(58) Field of Classification Search
CPC ............. A61F 2/88; A61F 2/91; A61F 2/885; A61F 2220/0058; A61F 2002/823
USPC ................................. 623/1.16, 1.22
See application file for complete search history.

(56) References Cited

U.S. PATENT DOCUMENTS

| | | | | |
|---|---|---|---|---|
| 4,553,545 A | * | 11/1985 | Maass et al. | 606/198 |
| 4,760,849 A | | 8/1988 | Kropf | |
| 4,969,458 A | * | 11/1990 | Wiktor | 623/1.11 |
| 5,041,126 A | | 8/1991 | Gianturco | |
| 5,342,387 A | | 8/1994 | Summers | |
| 5,603,722 A | * | 2/1997 | Phan et al. | 623/1.18 |
| 5,607,445 A | | 3/1997 | Summers | |
| 5,607,478 A | * | 3/1997 | Lentz et al. | 623/23.69 |
| 5,632,771 A | * | 5/1997 | Boatman et al. | 623/1.15 |
| 5,643,314 A | * | 7/1997 | Carpenter et al. | 623/1.2 |
| 5,707,387 A | * | 1/1998 | Wijay | 623/1.2 |
| 5,772,668 A | | 6/1998 | Summers et al. | |
| 5,797,952 A | | 8/1998 | Klein | |
| 5,824,052 A | | 10/1998 | Khosravi et al. | |
| 6,053,943 A | * | 4/2000 | Edwin et al. | 623/1.25 |
| 6,080,191 A | * | 6/2000 | Summers | 623/1.22 |

(Continued)

FOREIGN PATENT DOCUMENTS

WO      WO 00/62711      10/2000

OTHER PUBLICATIONS

International Search Report dated Aug. 29, 2008 from corresponding International App. No. PCT/US 08/56082.

(Continued)

*Primary Examiner* — Thomas McEvoy
*Assistant Examiner* — Julie A Szpira
(74) *Attorney, Agent, or Firm* — James F. Hann; Haynes Beffel & Wolfeld LLP

(57) ABSTRACT

An implantable vascular prosthesis is provided for use in a wide range of applications wherein at least first and second helical sections having alternating directions of rotation are coupled to one another. The prosthesis is configured to conform to a vessel wall without substantially remodeling the vessel, and permits accurate deployment in a vessel without shifting or foreshortening.

18 Claims, 12 Drawing Sheets

(56) References Cited

U.S. PATENT DOCUMENTS

| | | | |
|---|---|---|---|
| 6,241,691 B1* | 6/2001 | Ferrera et al. | 600/585 |
| 6,409,752 B1 | 6/2002 | Boatman et al. | |
| 6,425,915 B1* | 7/2002 | Khosravi et al. | 623/1.22 |
| 6,488,700 B2* | 12/2002 | Klumb et al. | 623/1.12 |
| 6,514,285 B1 | 2/2003 | Pinchasik | |
| 6,562,064 B1 | 5/2003 | deBeer | |
| 6,572,648 B1 | 6/2003 | Klumb et al. | |
| 6,607,551 B1 | 8/2003 | Sullivan et al. | |
| 6,645,237 B2 | 11/2003 | Klumb et al. | |
| 6,692,521 B2* | 2/2004 | Pinchasik | 623/1.12 |
| 7,169,175 B2 | 1/2007 | Cottone, Jr. et al. | |
| 7,410,498 B2* | 8/2008 | Penhasi | 623/1.22 |
| 2002/0151956 A1 | 10/2002 | Chobotov et al. | |
| 2003/0055484 A1* | 3/2003 | Lau et al. | 623/1.13 |
| 2004/0073293 A1* | 4/2004 | Thompson | 623/1.19 |
| 2004/0122504 A1 | 6/2004 | Hogendijk | |
| 2004/0186556 A1* | 9/2004 | Hogendijk et al. | 623/1.16 |
| 2004/0186557 A1* | 9/2004 | Gambale et al. | 623/1.22 |
| 2005/0165469 A1* | 7/2005 | Hogendijk | 623/1.15 |
| 2006/0030934 A1* | 2/2006 | Hogendijk et al. | 623/1.22 |
| 2006/0079955 A1 | 4/2006 | Brown | |
| 2006/0129233 A1* | 6/2006 | Eder et al. | 623/1.22 |
| 2006/0136033 A1 | 6/2006 | Hermann et al. | |
| 2006/0136035 A1 | 6/2006 | Hermann et al. | |
| 2007/0208416 A1 | 9/2007 | Burpee et al. | |

OTHER PUBLICATIONS

Office Action mailed Sep. 30, 2009 in corresponding U.S. Appl. No. 10/746,668, filed Dec. 23, 2003; 5 pages.

* cited by examiner

VASCULAR PROSTHESIS AND METHODS OF USE

FIELD OF THE INVENTION

The present invention relates to an implantable vascular prosthesis configured for use in a wide range of applications, and more specifically, to a prosthesis having an alternating helical section.

BACKGROUND OF THE INVENTION

Today there are a wide range of intravascular prostheses on the market for use in the treatment of aneurysms, stenoses, and other vascular irregularities. Balloon expandable and self-expanding stents are well known for restoring patency in a stenosed vessel, e.g., after an angioplasty procedure, and the use of coils and stents are known techniques for treating aneurysms.

Previously-known self-expanding stents generally are retained in a contracted delivery configuration using an outer sheath, then self-expand when the sheath is retracted. Such stents commonly have several drawbacks, for example, the stents may experience large length changes during expansion (referred to as "foreshortening" or "jumping") and may shift within the vessel prior to engaging the vessel wall, resulting in improper placement. Another disadvantage is that after the stent is deployed it can experience longitudinal movement within the vessel (also referred to as "migration"), which can be attributed to repetitive longitudinal loading and unloading of the stent.

Additionally, repetitive loading and unloading of a stent have also been known to cause fatigue induced strut failure, which may contribute to restenosis and subsequent vessel narrowing and/or occlusion. Additionally, many self-expanding stents have relatively large delivery profiles because the configuration of their struts limits further compression of the stent. Accordingly, such stents may not be suitable for use in smaller vessels, such as cerebral vessels and coronary arteries.

For example, PCT Publication WO 00/62711 to Rivelli describes a stent comprising a helical mesh coil having a plurality of turns and including a lattice having a multiplicity of pores. The lattice is tapered along its length. In operation, the plurality of turns are wound into a reduced diameter helical shape, and then constrained within a delivery sheath. The delivery sheath is retracted to expose the distal portion of the stent and anchor the distal end of the stent. As the delivery sheath is further retracted, subsequent individual turns of the stent unwind to conform to the diameter of the vessel wall.

The stent described in the foregoing publication has several drawbacks. For example, due to friction between the turns and the sheath, the individual turns of the stent may "bunch up," or overlap with one another, when the delivery sheath is retracted. In addition, once the sheath is fully retracted, the turns may shift within the vessel prior to engaging the vessel wall, resulting in improper placement of the stent. Moreover, because the distal portion of the stent may provide insufficient engagement with the vessel wall during subsequent retraction of the remainder of the sheath, ambiguity concerning accuracy of the stent placement may arise.

In another example, U.S. Pat. No. 5,603,722 to Phan et al. describes a stent formed of expandable strip-like segments. The strip-like segments are joined along side regions in a ladder-like fashion along offsetting side regions. A shortcoming of such a stent is that the junctions between adjacent segments are not provided with a means of addressing longitudinal loading. As a result, such a stent is susceptible to strut fracture.

In another example, U.S. Pat. No. 5,607,445 to Summers describes a balloon expandable stent. In one embodiment, the stent is constructed from a single wire that is configured so that each half of the wire is zig-zagged and curved to generally form a half-cylinder. The zig-zags of each half-cylinder are intermeshed so that they combine to form a cylindrical stent. The stent described in the foregoing publication has several drawbacks. The stent does not allow for longitudinal loading. As a result, applying a longitudinal load will cause the bends to move radially inward which will bias them into the vessel flow. Additionally, the stent design may be susceptible to fracture with repetitive loading and unloading.

In yet another example, U.S. Pat. No. 5,707,387 to Wijay describes a stent constructed from a plurality of bands, where each band is composed of a solid wire-like material formed into a closed, substantially rectangular shape. Each band is circumferentially offset from the adjacent band and adjacent bands are connected by one or more cross-tie members. This stent also has several drawbacks. The rectangular cell design does not allow for longitudinal loading because the cells are not flexible. Therefore, under a longitudinal load the apex will move out of plane and will be biased into the vessel (i.e., into the vessel flow). Secondly the stent may be susceptible to fracture with repetitive loading and unloading because of the rigid cells.

When utilizing stents in interventional procedures, it may be advantageous to deliver therapeutic agents to a vessel wall via the surface of the stent. Drug eluting stents have many advantages, such as controlled delivery of therapeutic agents over an extended period of time without the need for intervention, and reduced rates of restenosis after angioplasty procedures. Typically, the drug is disposed in the matrix of a bioabsorbable polymer coated on an exterior surface of the struts of the stents, and then gradually released into a vessel wall. The quantity of the therapeutic agent provided by the stent generally is limited by the surface area of the struts. Increasing the surface area of the struts may enhance drug delivery capability, but may compromise the overall delivery profile of the stent. There therefore exists a need for a prosthesis having a reduced delivery profile and enhanced drug delivery capabilities. This is especially beneficial if other attributes such as radial strength and flexibility are not compromised.

In view of the drawbacks of previously known devices, it would be desirable to provide apparatus and methods for an implantable vascular prosthesis comprising a plurality of helical portions joined together, wherein the prosthesis is configured to be used in a wide range of applications including maintaining patency in a vessel and delivering drugs to a vessel.

It also would be desirable to provide apparatus and methods for a vascular prosthesis that is flexible enough to conform to a natural shape of a vessel without substantially remodeling the vessel.

It further would be desirable to provide apparatus and methods for a vascular prosthesis having one or more optional radially expanding anchors that allow for additional control over the deployment of the vascular prosthesis at a desired location within a vessel.

It still further would be desirable to provide apparatus and methods for a vascular prosthesis that has a surface area that may be selected to facilitate in-vivo delivery of therapeutic agents without adversely impacting the mechanical properties (e.g., radial strength, flexibility, etc.) of the prosthesis.

It additionally would be desirable to provide apparatus and methods for a vascular prosthesis that has a strut configuration that allows for repetitive longitudinal loading and unloading of the prosthesis.

It further would be desirable to provide apparatus and methods for a vascular prosthesis that has a structure having the ability to absorb or distribute loads.

It yet further would be desirable to provide apparatus and methods for a vascular prosthesis that has a small delivery configuration to allow the prosthesis to be used in smaller vessels.

SUMMARY OF THE INVENTION

In view of the foregoing, it is an object of the present invention to provide apparatus and methods for an implantable vascular prosthesis comprising a plurality of helical stent portions having alternating directions of rotation joined together, wherein the prosthesis is configured to be used in a wide range of applications including, but not limited to, maintaining patency in a vessel and delivering drugs to a vessel.

It is a further object of the present invention to provide apparatus and methods for a vascular prosthesis that is flexible enough to conform to a natural shape of a vessel without substantially remodeling the vessel.

It is another object of the present invention to provide apparatus and methods for a vascular prosthesis having at least one alternating helical section that allows for controlled deployment of the vascular prosthesis at a desired location within a vessel.

It is another object of the present invention to provide apparatus and methods for a vascular prosthesis having a strut configuration that dampens the stresses associated with repetitive longitudinal loading and unloading, torsional loads, buckling and bending.

It is another object of the present invention to provide apparatus and methods for a vascular prosthesis having independent cells that absorb and/or distribute loads applied to the prosthesis.

It is a further object of the present invention to provide apparatus and methods for a vascular prosthesis that has a surface area that facilitates in-vivo delivery of therapeutic agents.

It is a further object of the present invention to provide apparatus and methods for a vascular prosthesis that has a small delivery configuration to allow the prosthesis to be used in smaller vessels.

These and other objects of the present invention are accomplished by providing a vascular prosthesis comprising a plurality of helical portions having alternating directions of rotation that are joined together. The helical portions may have different length, pitch and/or ribbon width to tailor the flexibility and circumferential vessel wall coverage as desired. The prosthesis is configured to engage a vessel wall and adapt to a natural curvature of the vessel. The vascular prosthesis may be used in a wide range of applications.

In an embodiment, the vascular prosthesis comprises a shape memory material, such as Nitinol, and includes an alternating helical section. As used in this specification, an "alternating helical section" is formed of two or more helical portions that are joined together and have at least one change in direction of rotation of the helices.

Prostheses of the present invention are delivered to a target vessel in a contracted state, constrained within an outer sheath, in which radially inwardly directed compressive forces may be applied by the outer sheath to the body of the prosthesis. In the contracted state, the helical section is wound down to a reduced diameter configuration, so that adjacent turns preferably partially overlap. As an alternative, the helical section may be configured so that there is no overlap if desired. As a still further alternative, the helical section may be compressed radially to a reduced diameter configuration in addition to or in lieu of winding.

In a preferred method of operation of a prosthesis the alternating helical section is provided in its contracted state within an outer sheath and the prosthesis is fluoroscopically advanced into a selected vessel using techniques that are known in the art. The alternating helical section then is positioned adjacent a target region of a vessel, such as a stenosed region. The outer sheath then is retracted proximally to cause a helical portion(s) of the alternating helical section to self-deploy and engage the vessel wall at the target region. Advantageously, by overlapping portions of the alternating helical section, the alternating helical section will expand in a unique controlled manner. This technique ensures that the prosthesis will not shift within the vessel during deployment.

The vascular prosthesis of the present invention is flexible enough to conform to the shape of a vessel without substantially remodeling the vessel.

Additionally, the mesh configuration of the alternating helical section preferably conforms to the vasculature of the target region since each of the plurality of turns is free to assume a curved configuration substantially independently of one another. Also, because the alternating helical section of the vascular prosthesis has a ribbon-like helical structure, it may be rolled down to a contracted state with a more accurate reduced delivery profile, compared to slotted-tube stents. This feature makes the stent of the present invention especially useful for treating defects in smaller vessels, such as cerebral arteries.

In accordance with another aspect of the present invention, the plurality of turns of the alternating helical section may comprise a substantially increased surface area relative to conventional stents that have a plurality of interconnected struts. The increased surface area of the turns is particularly advantageous for localized drug delivery. The turns may be coated with a drug-laden polymer coating or, alternatively, one or more dimples or through-holes may be disposed in a lateral surface of the turns to elute drugs over an extended period of time.

Methods of using the vascular prosthesis of the present invention, for example, in the treatment of the peripheral vasculature, also are provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The vascular prosthesis, according to the present invention, has an alternating helix configuration that provides a more accurate reduced delivery profile than previously known devices. Additionally, the prosthesis is configured to conform to a vessel wall without substantially remodelling the vessel, to provide improved compression resistance, deployment accuracy, migration resistance, radial strength and load dampening characteristics.

Figure 1:
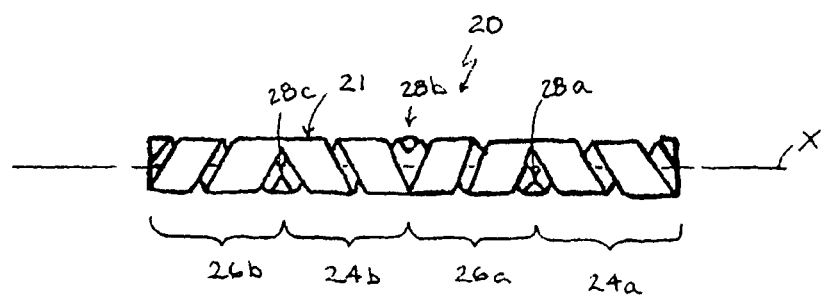
FIG. 1 is a schematic representation of a vascular prosthesis of the present invention in a deployed state.
Figure 2:
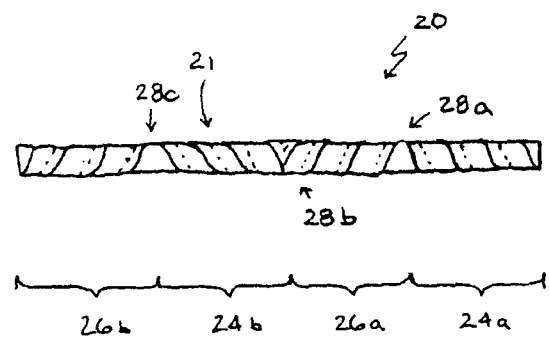
FIG. 2 is a schematic representation of the vascular prosthesis of the present invention in a contracted state.

Referring now to FIGS. 1 and 2, a schematic representation of a vascular prosthesis constructed in accordance with principles of the present invention is described. Vascular prosthesis ("stent") 20 illustratively comprises alternating helical section 21 capable of assuming contracted and deployed states. In FIG. 1, alternating helical section 21 is depicted in the deployed state.

Alternating helical section 21 is constructed from two or more helical portions having at least one change in the direction of rotation of the helices, and being joined at apex portions where the directions of rotation of adjacent helices change. In particular, first (i.e., proximal-most) helical portion 24a has a generally clockwise rotation about longitudinal axis X of prosthesis 20. Helical portion 26a adjoins the distal end of helical portion 24a at apex 28a and has a generally counter-clockwise rotation about longitudinal axis X. Helical portion 24b adjoins the distal end of helical portion 26a at apex 28b, and in turn is coupled to the proximal end of helical portion 26b at apex 28c. As a result of the alternating direction of rotation of the adjoining helical portions 24a, 26a, 24b and 26b of vascular prosthesis 20 includes three apices 28a, 28b and 28c that are oriented such that they point in alternating directions about the circumference of vascular prosthesis 20, generally in a plane that is normal to longitudinal axis X of vascular prosthesis 20. Preferably, each helical portion includes at least one full helical turn between adjacent apices. However, each helical portion may include more or less turns between adjacent apices, for example a helical portion may include 0.5-2.0 helical turns between adjacent apices.

The terminal ends of the alternating helical section may have any desired configuration. For example, as shown in FIG. 1, the terminal ends, or tails, of alternating helical section 21 are cut along a plane that is perpendicular to the longitudinal axis of vascular prosthesis 20. Alternatively, the terminal ends may be cut along any plane, such as for example parallel to the longitudinal axis. The terminal ends may end in a pointed or rounded tip or they may be truncated. As a further alternative, the width of the ribbon or mesh that forms the terminal helical portions may be varied. For example, the width of the ribbon of the terminal helical portion may taper so that it has the largest width adjacent the nearest apex and the smallest width near the terminal end. These features may be selected to provide a desired transitional flexibility at the ends of the alternating helical portion. That transitional flexibility may be used to assure that the curvature of a vessel remains smooth near the end of the stent.

A significant advantage of alternating helical section 21 as compared to other vascular prosthesis structures, is that apices 28 of alternating helical section 21 provide additional anchoring force at discrete locations along the length of alternating helical section 21. That anchoring force may be used to increase the radial force applied by the vascular prosthesis to a vessel wall as well as providing additional migration resistance. That anchoring force may be increased if desired by flaring out the ends and/or apices of the alternating helical section. Those portions may be flared outward by applying expansion and heat treatment so that those portions have a larger expanded diameter than the remainder of alternating helical section 21. Additionally, the alternating helical configuration allows the wall thickness of the device to be reduced because the design provides increased radial strength.

Alternating helical section 21 preferably is formed from a solid tubular member comprised of a shape memory material, such as nickel-titanium alloy (commonly known in the art as Nitinol). However, it should be appreciated that alternating helical section 21 may be constructed from any suitable material recognized in the art. The solid tubular member then is laser cut, using techniques that are known in the art, to define a specific pattern or geometry in the deployed configuration. Preferably, alternating helical section 21 is cut from the tube so that helical portions 24a, 26a, 24b, 26b are integrally formed as a single monolithic body. However, it should be appreciated that separate helical portions may be mechanically coupled, such as by welding, soldering or installing mechanical fasteners to construct alternating helical section 21. An appropriate expansion and heat treatment then may be applied to alternating helical section 21 of vascular prosthesis 20 so that the device may be configured to self-deploy from a contracted, delivery configuration to the deployed configuration.

Referring now to FIG. 2, vascular prosthesis 20 is shown in the contracted, delivery configuration, wherein alternating helical section 21 is in the contracted, reduced diameter state. Alternating helical section 21, however, is placed in the contracted state by winding helical portions 24, 26 about longitudinal axis X. In FIG. 2, apices 28a and 28c may be temporarily engaged to the inner shaft of a delivery catheter, and the shaft is rotated while apex 28b and the distal and proximal ends of alternating helical section 21 are held stationary.

Consequently, apices 28a and 28c are tightly wound onto the shaft of the delivery catheter and the remainder of each helical portion 24, 26 is wound against the shaft so that each turn of each portion 24, 26 overlaps an adjacent turn. For example, in some embodiments, approximately ⅔ of a layer is overlapped by the next layer. As a result, apex 28b and the distal and proximal ends of alternating helical section 21 are located furthest radially outward on the rolled alternating helical section 21. The overlap of the turns of helical portions 24, 26 are indicated by dashed lines in FIG. 2. The overlapping turns of alternating helical section 21 thus secure apices 28a and 28c when vascular prosthesis 20 is disposed within a delivery system.

Figure 3:
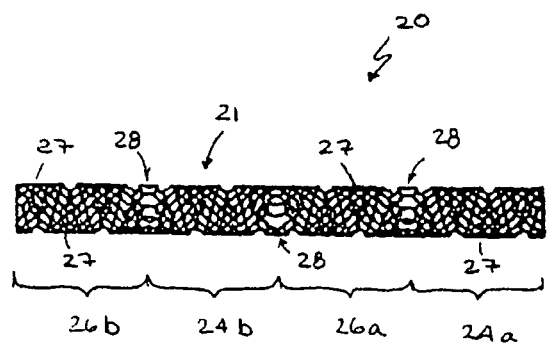
FIG. 3 is a side view of a vascular prosthesis of the present invention.
Figure 4:
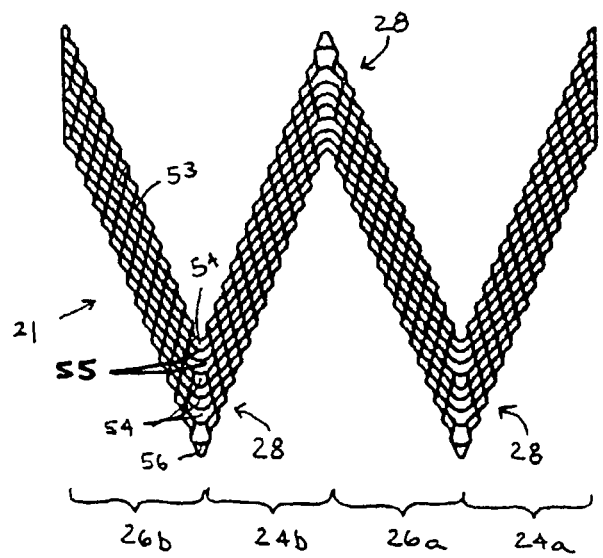
FIG. 4 is a schematic representation of the vascular prosthesis of FIG. 3 shown in a flattened configuration.

Referring now to FIGS. 3 and 4, an embodiment of vascular prosthesis 20, constructed in accordance with principles of the present invention, is described. It should be appreciated that FIG. 4 is a schematic view of vascular prosthesis 20 as it would appear if it were flattened. The components of vascular prosthesis 20 are identical to those depicted in FIGS. 1 and 2 and identical reference numbers are employed in the following description.

Alternating helical section 21 preferably comprises a helical mesh configuration including two or more helical portions 27. Helical portions 27 may include multiplicity of openings 53, 54, 56 of different shapes and sizes. The shape, size and orientation of any particular opening is selected to provide a desired response to longitudinal loads and also may be dependent upon the location of the openings within the mesh structure. The shape, size and orientation of the openings may also be selected to provide desired deployment, unwrapping, radial force and surface area coverage characteristics.

As shown in FIG. 4, alternating helical section 21 includes diamond-shaped openings 53 of generally equal size through the majority of each helical portion 24, 26. Additionally, the prosthesis of FIGS. 3 and 4 includes a curved, or wavy, edge which may provide benefits such as improved metal coverage and interlocking. For example, relative sliding of the portions of a wavy alternating helical section may provide a ratchet effect so that the overlapping portions may be incrementally and temporarily interlocked during deployment.

A wide variety of openings may be employed at apices 28a, 28b and 28c, where the helical portions adjoin adjacent helical portions. The openings may have any shape and/or size desired. Some designs include diamond, polygon, circles, ellipses, elongated diamonds, etc. In addition, the openings of apices 28 need not be symmetric with respect to a centerline of apex 28. It should be appreciated that the size, shape and orientation of any of the openings may be selected so that in the deployed state some struts may bow radially outward or inward so that they interlock with adjacent, overlapping openings.

In FIG. 4, each apex includes plurality of openings 54 and one tip opening 56 that forms a tip of the respective apex, which may be triangular as shown. Openings 54 are defined by struts 55 that extend between adjacent helical portions 24, 26.

Figure 5:
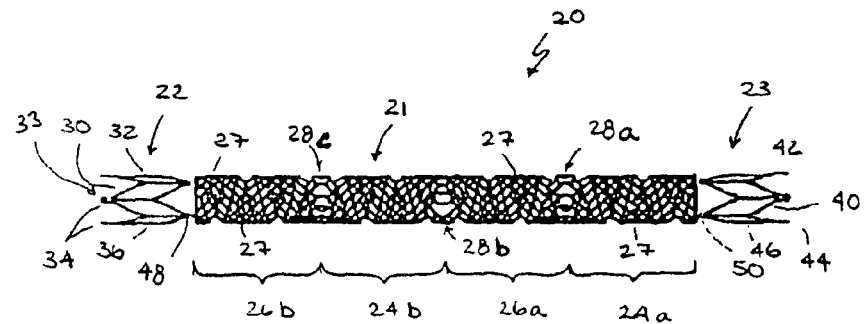
FIG. 5 is a side view of a vascular prosthesis of the present invention that includes optional distal and proximal anchors.
Figure 6:
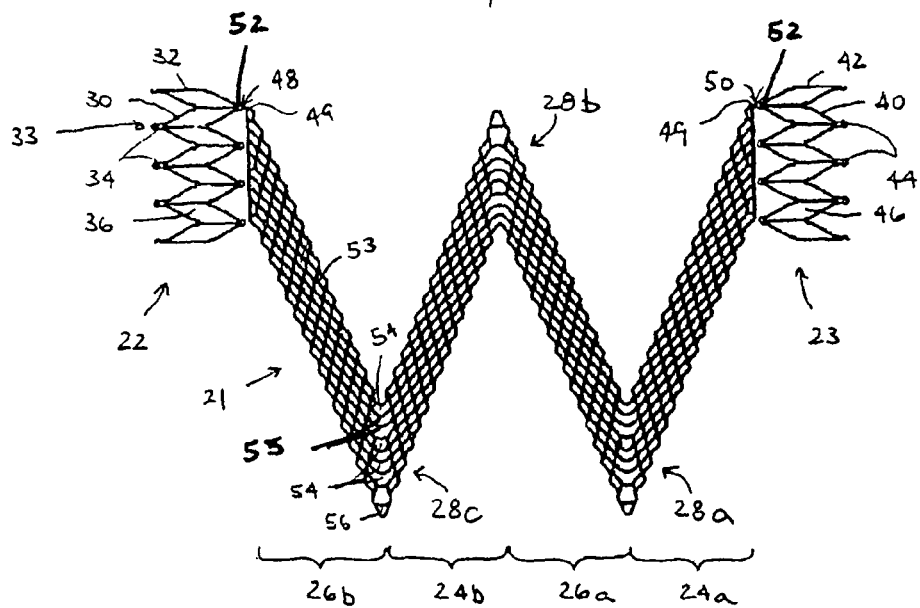
FIG. 6 is a schematic representation of the vascular prosthesis of FIG. 5 shown in a flattened configuration.

Referring to FIGS. 5 and 6, another embodiment of vascular prosthesis 20 is shown, which includes optional distal and proximal anchor sections 22, 23. Distal anchor section 22 preferably is a tubular mesh structure that is coupled to a distal end of alternating helical section 21. In particular, distal anchor section 22 includes a pair of concentrically aligned zig-zag rings 30 that are spaced from one another and coupled by struts 32. Struts 32 extend between corresponding apices 34 of rings 30 and are oriented parallel to a longitudinal axis of vascular prosthesis 20. Apices 34 may comprise one or more radiopaque markers 33 such as a radiopaque marker band or coating. As a result, rings 30 and struts 32 combine to define a plurality of openings 36 shaped as parallelograms, thereby forming a tubular mesh. The tubular mesh preferably is formed by laser cutting a solid tube.

Distal anchor section 22 preferably is formed from a solid tubular member comprising a shape memory material, such as nickel-titanium alloy, which is laser cut, using techniques that are known in the art, to a desired deployed configuration. Preferably, distal anchor section 22 is cut from the tube so that rings 30 and struts 32 are formed as a single monolithic body.

However, it should be appreciated that distal anchor section 22 may be constructed from separate rings 30 and struts that are mechanically coupled in a secondary operation, such as by welding, soldering or employing a mechanical fastener, such as a rivet. An appropriate heat treatment then may be applied so that distal anchor section 22 may be configured to self-deploy radially outward from a contracted, delivery configuration to a deployed configuration in conjunction with alternating helical section 21, described above. Alternatively, distal anchor section 22 may be configured to be balloon expandable.

Proximal anchor section 23 also preferably has a tubular mesh construction. Proximal anchor section 23 includes a pair of concentrically aligned zig-zag rings 40 that are spaced from one another and coupled by struts 42. Struts 42 extend between corresponding apices 44. Apices 44 may comprise one or more radiopaque markers 43 such as a radiopaque marker, band or coating. Rings 40 are oriented parallel to longitudinal axis X of vascular prosthesis 20. Rings 40 and struts 42 combine to define a plurality of openings 46 shaped as parallelograms. Similar to distal anchor section 22, the tubular mesh structure of proximal anchor section 23 preferably is formed by laser cutting a solid tube. Proximal anchor section 23 may be constructed in the same manner described above with respect to distal anchor section 22. Alternatively, proximal anchor section 23 also may be constructed to be balloon expandable.

Moreover, distal anchor section 22 and proximal anchor section 23 may have different constructions. Although distal anchor section 22 and proximal anchor section 23 as described above are identical, they alternatively may have different zig-zag or cell structures or deployment modes (e.g., self-expanding at the distal end and balloon expandable at the proximal end). For example, anchor sections 22, 23 may be constructed as a single zig-zag ring. As a further alternative, anchor sections 22, 23 may be configured so that openings 36, 46 have shapes other than parallelograms, e.g., openings 36, 46 may be shaped as diamonds or any other polygonal shape, circles or ellipses. Furthermore, although anchor sections 22, 23 are illustrated as including struts 32, 42 extending between each set of corresponding apices, struts 32, 42 may extend between fewer sets of corresponding apices. For example, as shown in FIG. 7, struts may extend between relatively few apices. In addition, the distance between the zig-zag rings of anchor sections 22, 23 may also be selected to provide an anchor section of any desired length.

Furthermore, the outer edges of anchor sections 22, 23 may be biased so that the proximal-most edge of anchor section 23 and the distal-most edge of anchor section 22 expand further radially outward than with respect to longitudinal axis X than the remainder of the anchor section. This configuration may be useful to increase radial outward force upon a patient's vessel and thus improve anchoring of vascular prosthesis 20 within the vessel. Such a biased configuration may be established by heat-treating a shape memory material using techniques that are known in the art.

Distal anchor section 22 is coupled to the distal end of alternating helical section 21 at junction 48. Similarly, proximal anchor section 23 is coupled to the proximal end of alternating helical section 21 at junction 50. Preferably, junctions 48, 50 are formed from a strut of alternating helical section 21 that extends from that section and is coupled to a portion of the adjacent zig-zag rings 30, 40 of the respective anchor section 22, 23.

Junctions 48, 50 may comprise one or more radiopaque markers 52 such as a radiopaque marker band or coating. Radiopaque marker 52 facilitates positioning of junctions 48, 50 at a desired longitudinal position within a patient's vessel, and further facilitates alignment of vascular prosthesis 20 at a desired axial orientation within the vessel. For example, radiopaque markers 52 may be used to orient alternating helical section 21 so that a desired lateral surface of alternating helical section 21 deploys to overlay the diseased vessel segment.

It will be apparent to those skilled in the art that junctions 48, 50 may comprise other strut arrangements to connect distal anchor section 22 and proximal anchor section 23 to alternating helical section 21. For example, more than one strut may extend from alternating helical section 21 to a respective anchor 22, 23.

Various alternate junction configurations will be described which may be used to couple distal anchor section 22 and/or proximal anchor section 23 to alternating helical section 21. As described above and as shown in FIGS. 5 and 6, anchors 22, 23 are coupled to alternating helical section 21 by one or more struts 49. Struts 49 may be any desired length and may extend to any portion of the adjacent anchor. For example, struts 49 may extend to an apex 34 of anchor 22 or any other portion of anchor 22. In addition, struts 49 may extend from any portion of alternating helical section 21 near an end of the section. For example, as shown in FIG. 6, strut 49 extends from a tip of alternating helical section 21. Alternatively, struts 49 may extend from a portion of alternating helical section 21 away from the tip.

In one preferred embodiment, alternating helical section 21, distal anchor section 22 and proximal anchor section 23 are integrally formed as a single monolithic body, such as by laser cutting all three components from a single tube. In such a construction of vascular prosthesis 20, the struts extending from alternating helical section 21 that form junctions 48, 50 also may form struts 32, 42 of the respective anchor section 22, 23. Alternatively, anchor sections 22, 23 may be manufactured separately from alternating helical section 21 and mechanically coupled in a subsequent process, such as by soldering, welding, installing mechanical fasteners (e.g., rivets) or other means, as will be apparent to one skilled in the art.

Figure 7A:
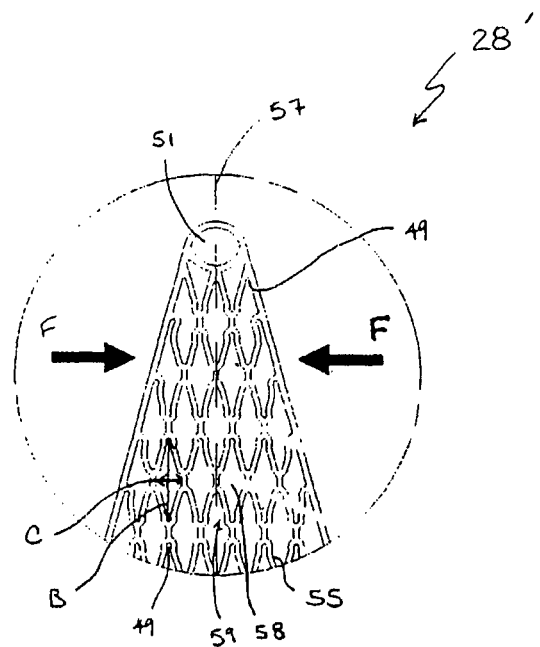
FIGS. 7A and 7B are side views of an apex portion of a vascular prosthesis according to the present invention.
Figure 7B:
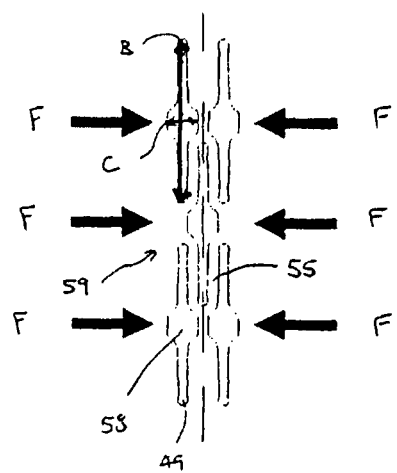

Referring to FIGS. 7A and 7B, an alternative strut configuration for the stent and particularly the apices of the vascular prosthesis is described. Apex 28' is constructed with struts 55 that form plurality of cells 59 defining elongate openings 58. Elongate openings 58 allow cells 59 to be compressed in response to longitudinal loads (shown by arrows F) placed on vascular prosthesis 20.

In addition, tip aperture 51, or eyelet, is included in apex 28'. Apertures 51 are provided so that apex 28' may be easily coupled to a delivery device, as will be described in greater detail below. As shown, aperture 51 is generally elliptical, but it should be appreciated that the shape of aperture 51 may be selected to correspond to the structure of the intended delivery device.

Elongate openings 58 each generally have major axis B corresponding to the longest distance across opening 58 and minor axis C corresponding to the shortest distance across opening 58. Referring to FIG. 12B, a portion of apex 28' of FIG. 12A is shown with cells 59 compressed under the influence of longitudinal force F. Elongate openings 58 are oriented so that major axis B of each opening 58 is parallel with center line 57 of apex 28' and minor axis C of each opening 58 is perpendicular to center line 57. During compression minor axis C is reduced while major axis B remains generally unchanged. As a result, the longitudinal load may be dampened by compression of the mesh structure of vascular prosthesis 20.

Elongate openings 58 preferably are shaped to reduce stress concentration. In the present embodiment, elongate openings 58 are generally diamond-shaped with rounded corners 49 at the junctions of adjacent struts 55. It should be appreciated that elongate openings may be any elongate shape. The size, shape and orientation of cells 59 on either side of center line 57 are shown generally identical. With such a configuration, dampening occurs equally from both sides of center line 57 when a longitudinal load is applied. However, it should be appreciated that the dampening characteristics of vascular prosthesis 20 may be tailored by including cells having different size, shape and/or orientation on either or both sides of center line 57. It is also noted that the helical portions of the stent provide a significant level of additional dampening of forces, including torsional and buckling. Furthermore, it should be appreciated that the apices included throughout vascular prosthesis 20 need not be identical and may be configured to provide differing dampening characteristics throughout vascular prosthesis 20.

Figure 8A:
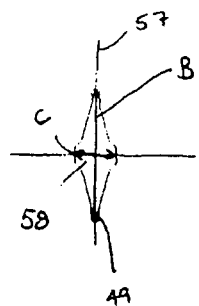
FIGS. 8A-8C are side views of a cell of a vascular prosthesis of the present invention having alternate orientations; invention.
Figure 8B:
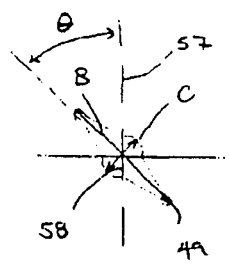
Figure 8C:
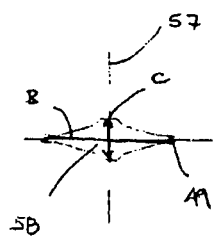

In addition, the orientation of openings 58 with respect to center line 57 and the longitudinal axis of vascular prosthesis may be selected to further control load dampening characteristics. Referring to FIGS. 8A-8C various exemplary orientations of openings 58 will be described. Openings 58 may be oriented so that major axis B is parallel to center line 57 as shown in FIG. 8A. In that orientation, cells 59 are configured so that longitudinal loading of a vascular prosthesis causes longitudinal compression. Openings 58 also may be oriented so that major axis B is angled with respect to center line 57. For example, as shown in FIG. 8B, opening 58 is oriented so that major axis B is rotated by angle θ from center line 57, which is approximately 45 degrees. In another embodiment, opening 58 may be oriented so that major axis B is perpendicular to center line 57 and as a result longitudinal forces may be redirected circumferentially through apex 28. It should be appreciated that the orientations of openings 58 also may be utilized throughout helical portions 24, 26 for openings 53 to distribute stress as desired. Additionally, a portion of openings 53, 54, 56, 58 may be replaced by fully covered portions, if desired, to provide additional surface area to interface a vessel wall, such as for drug delivery.

Figure 9:
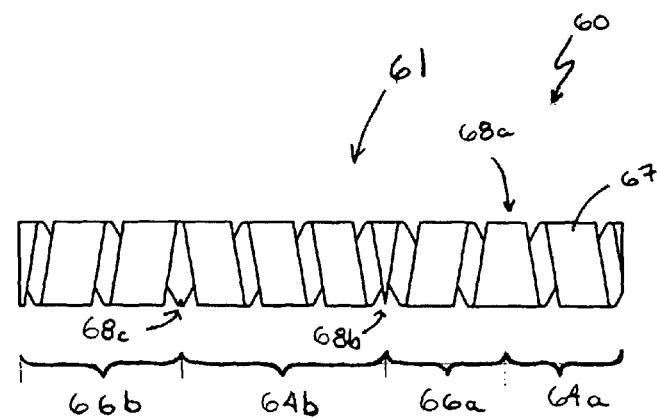
FIG. 9 is a schematic representation of another embodiment vascular prosthesis of the present invention in a deployed state.

Referring now to FIG. 9, vascular prosthesis 60 will be described. Vascular prosthesis 60 includes alternating helical section 61 formed from helical portions 64, 66 having different lengths. Alternating helical section 61 is constructed from helical portions 64, 66 having alternating directions of rotation that are joined at apices 68.

First (i.e., proximal-most) helical portion 64a has a generally clockwise rotation about longitudinal axis X of prosthesis 60 and a relatively short length that results in the portion having approximately one full turn 67 when vascular prosthesis 60 is deployed. Helical portion 66a adjoins the distal end of helical portion 64a at apex 68a and has a generally counter-clockwise rotation about longitudinal axis X. Helical portion 66a has a length that is approximately the same as the length of helical portion 64a resulting in helical portion 66a having approximately one full turn 67. Helical portion 64b adjoins the distal end of helical portion 66a at apex 68b, and in turn is coupled to the proximal end of helical portion 66b at apex 68c. The lengths of helical portions 64b and 66b are selected so that they have three and two full turns 67, respectfully. As a result of the alternating direction of rotation of the adjoining helical portions 64a, 66a, 64b and 66b, apices 68a, 68b and 68c are oriented such that they point in alternating directions about the circumference of vascular prosthesis 60, generally in a plane that is normal to longitudinal axis X of vascular prosthesis 60. In addition, the lengths of helical portions 64, 66 result in apices 68 being located at various locations around the circumference of vascular prosthesis 60. It will be appreciated that the lengths of helical portions 64, 66 may be selected so that apices are aligned if desired. It should be appreciated that the positioning of the apices may be selected to control gapping in a curved vessel. Additionally, the positioning of the apices may be selected to control the distribution of lower radial force apices around the vessel lumen to improve crush resistance and for control over flexibility.

Alternating helical section 61 preferably is formed from a solid tubular member comprised of a shape memory material, such as nickel-titanium alloy (commonly known in the art as Nitinol). However, it should be appreciated that alternating helical section 61 may be constructed from any suitable material and/or any suitable method as described above with regard to the previous embodiments.

Figure 10:
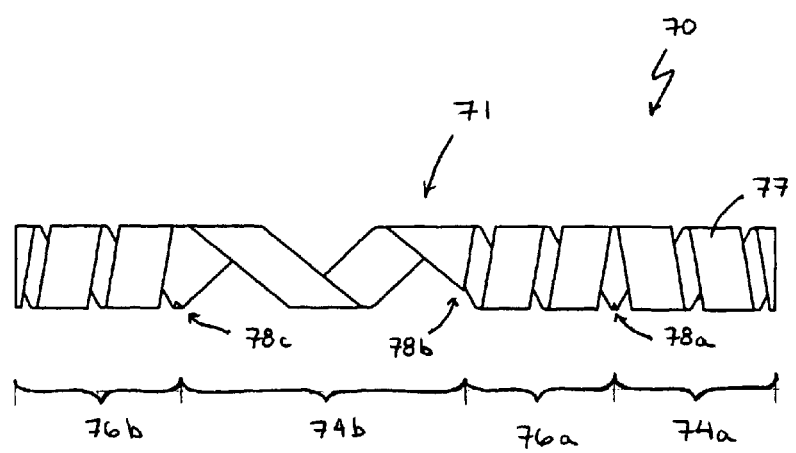
FIG. 10 is a schematic representation of another embodiment vascular prosthesis of the present invention in a deployed state.

Referring now to FIG. 10, vascular prosthesis 70 will be described. Vascular prosthesis 70 includes alternating helical section 71 formed from helical portions 74, 76 having different pitches (i.e., different ratios of number of turns per length). Alternating helical section 71 is constructed from helical portions 74, 76 having alternating directions of rotation that are joined at apices 78. Additionally, although prosthesis 70 is illustrated wherein the ribbons have constant width, it should be appreciated that the width of any portion of the prosthesis may be selected to provide a desired gap between adjacent turns or portions.

First (i.e., proximal-most) helical portion 74a has a generally clockwise rotation about longitudinal axis X of prosthesis 70 and a relatively high pitch that results in the portion having approximately two full turns 77 over its length when vascular prosthesis 70 is deployed. Helical portion 76a adjoins the distal end of helical portion 74a at apex 78a and has a generally counter-clockwise rotation about longitudinal axis X. Helical portion 76a has length and pitch that are approximately the same as the length and pitch of helical portion 74a. Helical portion 74b adjoins the distal end of helical portion 76a at apex 78b, and in turn is coupled to the proximal end of helical portion 76b at apex 78c. The pitch of helical portion 74b is selected so that it has one full turns 77 over a length approximately twice that of helical portion 74a, i.e., approximately ¼ the pitch of portion 74a. Helical portion 76b has a pitch that also is approximately the same as portion 74a. It will be appreciated, however, that any number of helical portions 74, 76 may have different pitches and the pitch for any portion may be selected for any desired flexibility. As a result of the alternating direction of rotation of the adjoining helical portions 74a, 76a, 74b and 76b, apices 78a, 78b and 78c are oriented such that they point in alternating directions about the circumference of vascular prosthesis 70, generally in a plane that is normal to longitudinal axis X of vascular prosthesis 70. It will be appreciated that the lengths and pitches of helical portions 74, 76 may be selected so that apices are aligned or located at various circumferential positions as desired, for example to provide desired flexibility, gap control and/or compression resistance.

Alternating helical section 71 preferably is formed from a solid tubular member comprised of a shape memory material, such as nickel-titanium alloy (commonly known in the art as Nitinol). However, it should be appreciated that alternating helical section 71 may be constructed from any suitable material and/or any suitable method as described above with regard to the previous embodiments.

Figure 11:
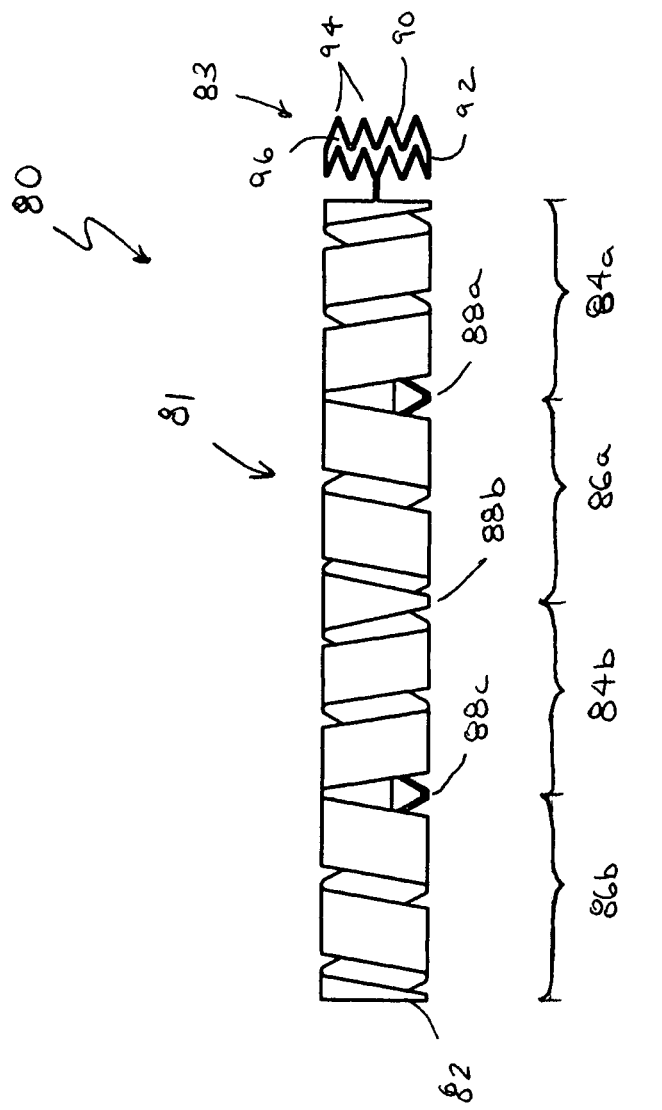
FIG. 11 is a schematic representation of another embodiment vascular prosthesis of the present invention in a deployed state.

Referring now to FIG. 11, vascular prosthesis 80 will be described. Vascular prosthesis 80 includes alternating helical section 81 formed from helical portions 84, 86 and proximal anchor 83. Alternating helical section 81 is constructed from helical portions 84, 86 having alternating directions of rotation that are joined at apices 88. The inclusion of one anchor 83 results in alternating helical section 81 having a tail 82, or free end. Alternating helical section 81 is configured so that tail 82 is located radially outward of the adjacent helical portion 86b when vascular prosthesis 80 is in a contracted state. The configuration may be selected to provide a desired behavior during deployment.

First (i.e., proximal-most) helical portion 84a is coupled to and extends distally of proximal anchor section 83 and has a generally clockwise rotation about longitudinal axis X of prosthesis 80. Helical portion 86a adjoins the distal end of helical portion 84a at apex 88a and has a generally counter-clockwise rotation about longitudinal axis X. Helical portion 84b adjoins the distal end of helical portion 86a at apex 88b, and in turn is coupled to the proximal end of helical portion 86b at apex 88c. As a result of the alternating direction of rotation of the adjoining helical portions 84a, 86a, 84b and 86b, apices 88a, 88b and 88c are oriented such that they point in alternating directions about the circumference of vascular prosthesis 80, generally in a plane that is normal to longitudinal axis X of vascular prosthesis 80.

Proximal anchor section 83 has a tubular mesh construction. Proximal anchor section 83 includes a pair of concentrically aligned zig-zag rings 90 that are spaced from one another and coupled by struts 92. Struts 92 extend between corresponding apices 94. Apices 94 may comprise one or more radiopaque features such as a radiopaque marker, band or coating. Rings 90 are oriented parallel to the longitudinal axis of vascular prosthesis 80. Rings 90 and struts 92 combine to define a plurality of zig-zag shaped openings 96. The tubular mesh structure of proximal anchor section 83 preferably is formed by laser cutting a solid tube.

Alternating helical section 81 preferably is formed from a solid tubular member comprised of a shape memory material, such as nickel-titanium alloy (commonly known in the art as Nitinol). However, it should be appreciated that alternating helical section 81 may be constructed from any suitable material and/or any suitable method as described above with regard to the previous embodiments.

Figure 12:
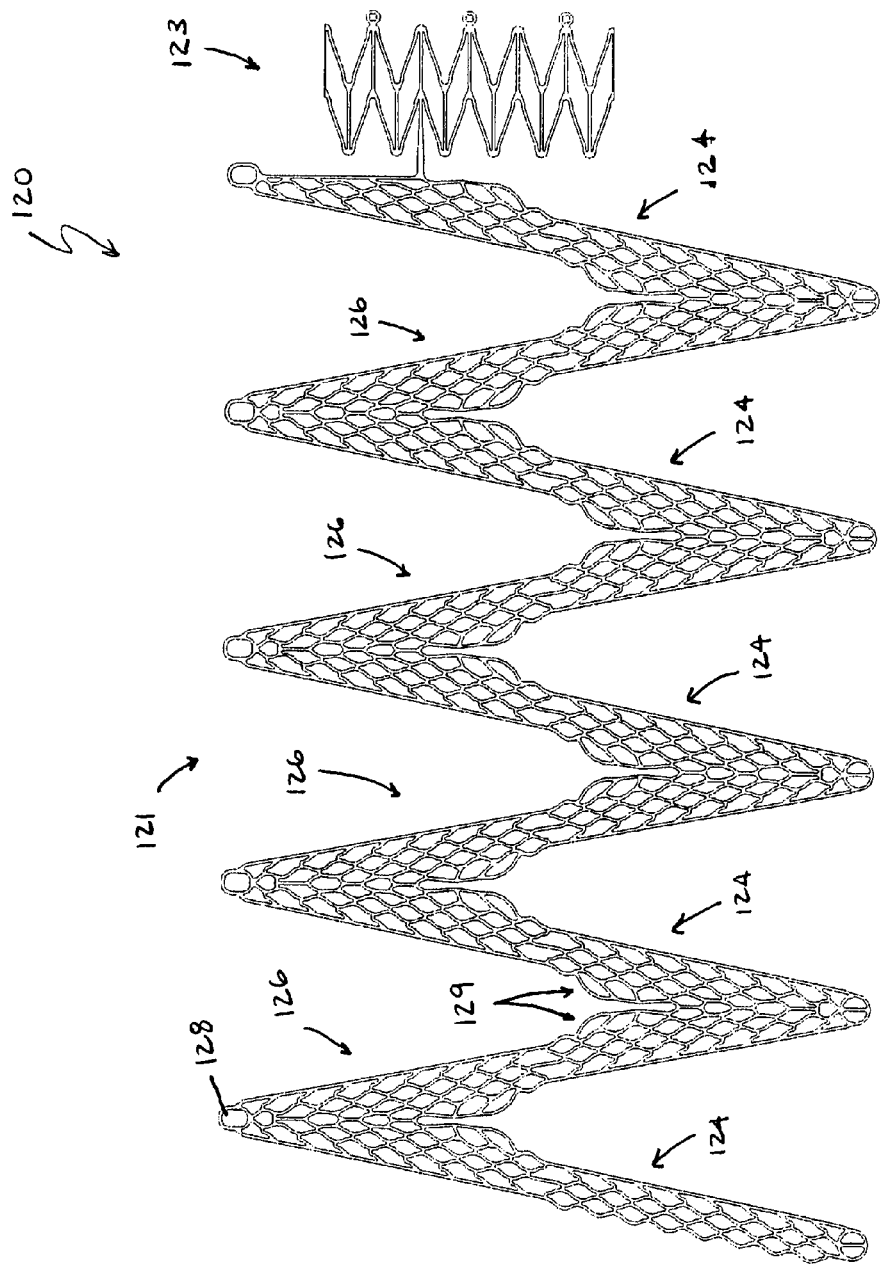
FIG. 12 is a schematic representation of another embodiment of the vascular prosthesis shown in a flattened configuration.
Figure 13:
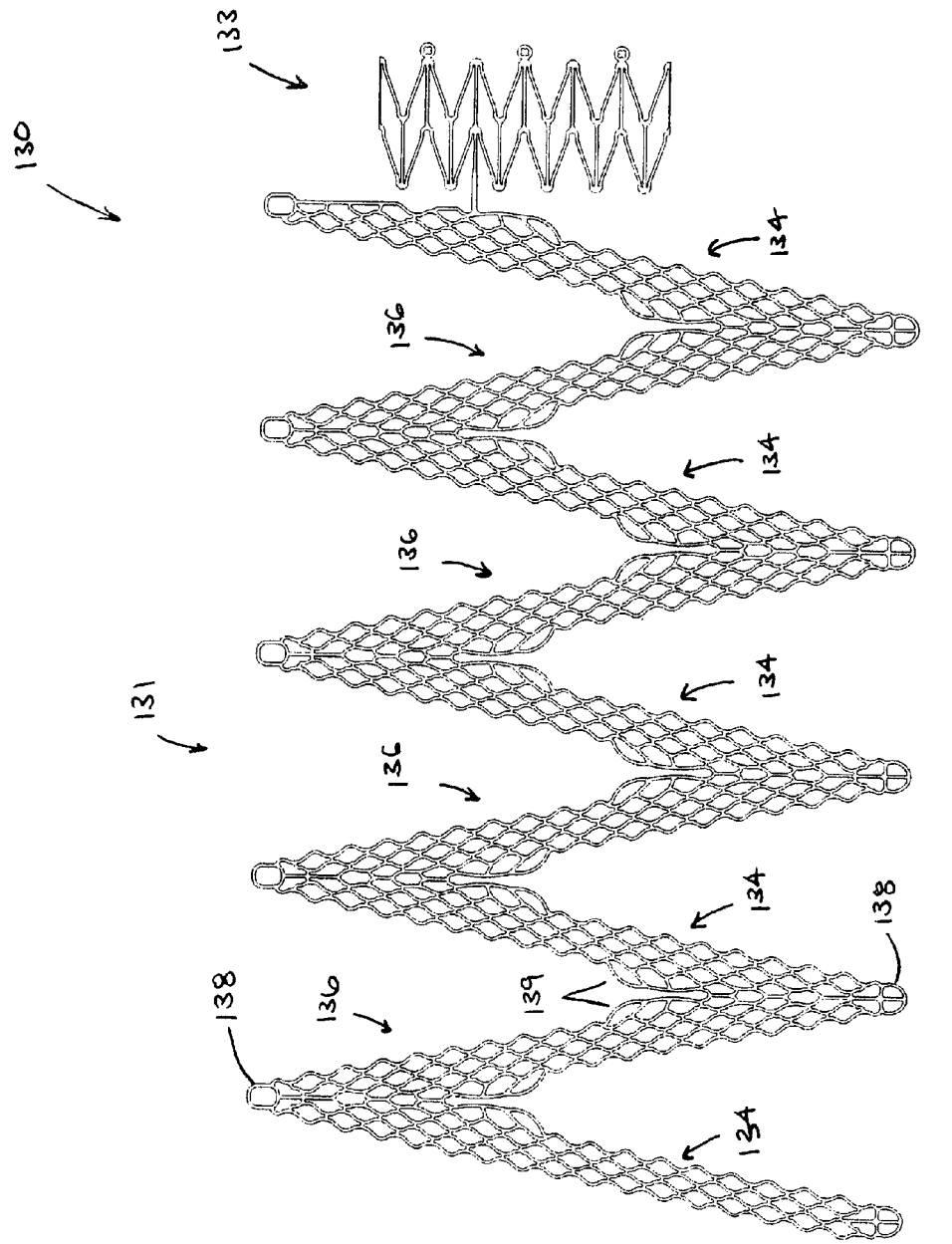
FIG. 13 is a schematic representation of another embodiment of the vascular prosthesis shown in a flattened configuration.

Referring to FIGS. 12 and 13, various embodiments of the vascular prosthesis having a single anchor will be described. In FIG. 12, vascular prosthesis 120 includes alternating helical section 121 and an optional proximal anchor section 123. Similar to the previously described embodiments, alternating helical section 121 is constructed from a plurality of helical portions 124, 126 that have alternating directions of rotation and that are joined at apices 128. Alternating helical section includes straight edges to help assure smooth deployment. In particular, the straight edges avoid interstices that may interlock when portions of alternating helical section 121 overlap. Alternating helical section 121 also includes flanges 129 that are configured to overlap apices 128 in both contracted and deployed states. The number of helical portions 124, 126 may be selected and apices 128 may be configured so that tail 122 is wrapped radially outward of the adjacent helical portion 124 when vascular prosthesis 120 is in a contracted state. However it should be appreciated that the number of portions and configuration of apices may be selected to that the tail is inner-wrapped.

In FIG. 13, vascular prosthesis 130 includes alternating helical section 131 and an optional proximal anchor section 133. Similar to the previously described embodiments, alternating helical section 131 is constructed from a plurality of helical portions 134, 136 that have alternating directions of rotation and that are joined at apices 138. Alternating helical section includes wavy edges. The wavy edge may be selected so that the shape and flexibility of the cells that form each helical portion may be tailored as desired. In addition, the wavy edges may be used so that portions of vascular prosthesis interlock when deployed. Alternating helical section 131 also includes flanges 139 that are configured to overlap apices 138 in both contracted and deployed states. In the present embodiment, the number of helical portions 134, 136 are selected and apices 138 are configured so that tail 132 is wrapped radially outward of the adjacent helical portion 134 when vascular prosthesis 130 is in a contracted state. However, it should be appreciated that the number of helical portions may be selected so that tail 132 is wrapped radially inward if desired. It will be appreciated that the apices configured to be located radially inward when the vascular prosthesis is in a contracted state are configured differently than the apices configured to be located radially outward as shown in FIGS. 12 and 13. The apices may be configured differently to simplify temporarily coupling the inwardly located apices to a delivery device while providing desired flexibility or radial force in the outwardly located apices.

As will be apparent to one skilled in the art, the configuration of the alternating helical sections depicted herein is merely for illustrative purposes. Any combination of covered portions and openings of any shape and size may be provided along the helical portions, as desired. Alternatively, one or more helical portions may be completely solid, such that the openings are omitted entirely from that portion. As a further alternative, the entire alternating helical section may be covered so that the device may be used as a stent graft. In such an embodiment, ePTFE and DACRON are examples of materials that may be used to cover the alternating helical section.

As will be apparent to those skilled in the art, a combination of solid regions and openings may be provided along the length of the alternating helical section, for example, to selectively increase surface area and drug delivery capabilities along the alternating helical section, or to influence flow dynamics within a vessel.

It will be appreciated that different drug delivery modalities may be used in conjunction with the vascular prosthesis of the present invention. For example, vascular prosthesis may include one or more dimples and/or through holes that may have a therapeutic agent disposed therein. As a further alternative, a therapeutic agent may be incorporated into the any of the openings previously described above. As a still further alternative, a therapeutic agent may be disposed in the matrix of a bioabsorbable polymer coated on any portion of the vascular prosthesis, and the drug may be gradually released into a localized region of a vessel wall.

One or more of the helical portions also may be selectively coated with an elastomeric polymer, such as polyurethane. The elastomeric polymer may partially or fully cover the selected portions. As a further alternative, the covering material may be included only in the openings of the mesh structure so that it fills the openings without increasing the overall diameter of the struts. For example, the elastomeric polymer may be disposed on a portion of the circumference of the alternating helical section, e.g., to reduce blood flow into a sac of the aneurysm. Additionally, a therapeutic agent may be disposed on the elastomeric polymer to increase the working surface area of the alternating helical section. Alternatively, the therapeutic agent may be disposed directly on the alternating helical section, either with or without the use of an elastomeric polymer.

The therapeutic agent may include, for example, antiplatelet drugs, anticoagulant drugs, antiproliferative drugs, agents used for purposes of providing gene therapy to a target region, or any other agent, and may be tailored for a particular application. Radiopaque markers (not shown) also may be selectively disposed on any portion of vascular prosthesis including in the vicinity of the therapeutic agents to facilitate alignment of the therapeutic agents with a target site of a vessel wall. Advantageously, higher doses of such agents may be provided using the vascular prosthesis of the present invention, relative to previously known coils or stents having interconnected struts, due to the increased surface area associated with the alternating helical section.

In operation, the overlap of portions of the alternating helical section when it is in the contracted state and the number of helical portions, causes alternating helical section 101 to deploy in a unique sequence, as will be described in greater detail below with reference to FIGS. 15A-15D. Advantageously, the order of deployment of the portions of alternating helical section 101 alleviates drawbacks associated with the prior art such as the tendency of the turns of the helical section to jump or shift during deployment and also results in the location of deployment being more easily controlled. Another benefit is that deployment of discrete segments may be more easily controlled. Additionally, the alternating helical section may be balloon expandable. In particular, the structure allows a user to post dilate discrete sections with a balloon. For example, a user may expand a selected portion of the device adjacent a specific apex.

Figure 14:
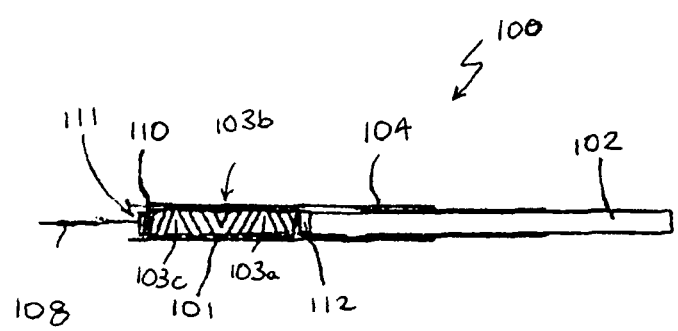
FIG. 14 is a cross-sectional view of a delivery system suitable for use in delivering the vascular prosthesis of FIG. 3.

In FIG. 14, a delivery system 100 suitable for use in delivering a vascular prosthesis of the present invention is described. Delivery system 100 comprises catheter body 102, outer sheath 104, and a lumen dimensioned for the passage of guidewire 108. Catheter body 102 preferably includes distal marker 111 and stop 110 located adjacent the distal end of alternating helical section 101 and proximal stop 112 located adjacent the proximal end of alternating helical section 101. It will be appreciated that additional stops may be employed when a vascular prosthesis having one or more anchors is delivered so that a stop may be provided between an anchor and the alternating helical section.

Distal stop 110 may comprise a raised ledge on catheter body 102 so that the distal end of alternating helical section 101 bears on the ledge to prevent relative movement between alternating helical section 101 and catheter body 102 in the distal direction. Alternatively, distal stop 110 may comprise a plurality of raised pins or knobs that prevent relative motion between alternating helical section 101 and catheter body 102 parallel to the longitudinal axis. Proximal stop 112 also may comprise a raised ledge, pins or knobs on catheter body 102, and both distal and proximal stops 110 and 112 may be radio-opaque, so as to be visible under a fluoroscope and provide a radiopaque marker. It should be appreciated that any portion of the delivery device or vascular prosthesis may include one or more radiopaque markers.

Vascular prosthesis 109 is collapsed onto catheter body 102 by winding alternating helical section 101 around catheter body 102. In order to wind alternating helical section 101 on catheter body 102, apices 103a and 103c may be temporarily coupled to catheter body 102 and the remainder of alternating helical section 101 is wound around catheter body 102 until it is collapsed as shown in FIG. 14.

After alternating helical section 101 is wound on catheter body 102, outer sheath 104 is advanced distally over catheter body 102 to capture alternating helical section 101 between catheter body 102 and outer sheath 104.

Figure 15A:
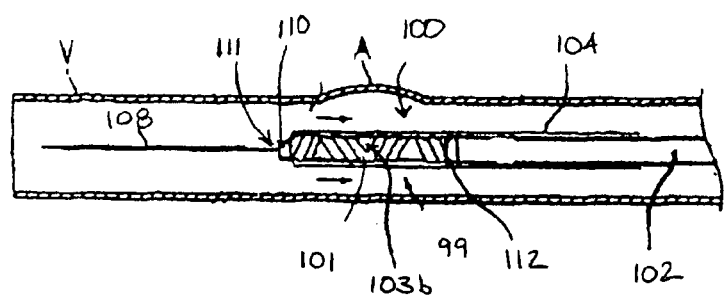
FIGS. 15A-15D are side sectional views illustrating use of the vascular prosthesis in the treatment of an aneurysm.

Referring to FIG. 15A, in operation, guidewire 108 is percutaneously and transluminally advanced through a patient's vasculature, using techniques that are known in the art. Guidewire 108 is advanced until a distal end of guidewire 108 is positioned distal of aneurysm A, which is situated in vessel V. Delivery system 100, having vascular prosthesis 109 contracted therein, then is advanced over guidewire 108 through the central lumen of catheter body 102. Delivery system 100 preferably is advanced under fluoroscopic guidance until distal marker 111 is situated distally to aneurysm A and alternating helical section 101 and apex 103b are situated adjacent to the aneurysm.

Once alternating helical section 101 is located adjacent to aneurysm A, outer sheath 104 is retracted proximally to cause alternating helical sections to deploy until outer sheath 104 is retracted to proximal stop 112.

Figure 15B:
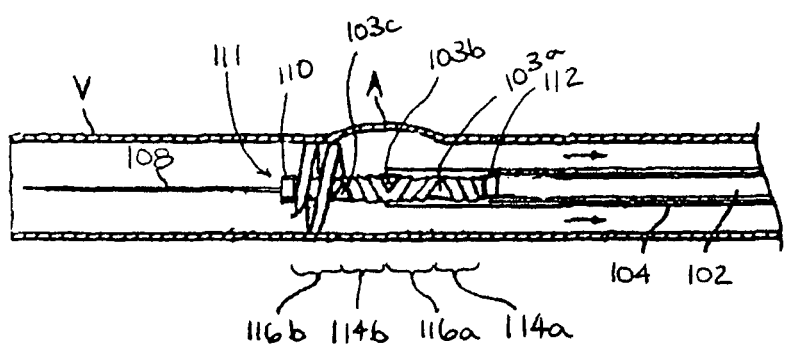
Figure 15C:
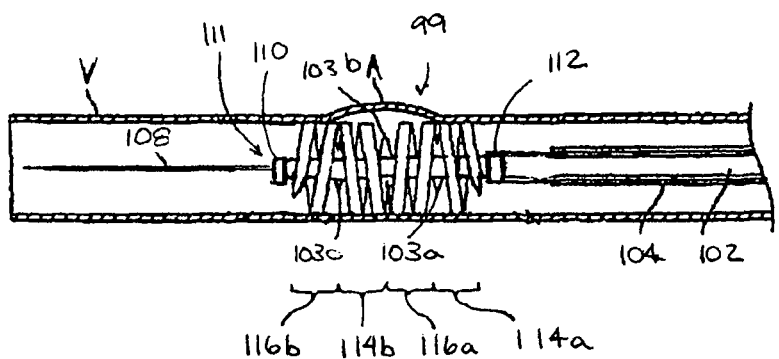

Referring to FIGS. 15B and 15C, after the distal end of alternating helical section 101 is secured distal of aneurysm A, outer sheath 104 is further retracted proximally to allow alternating helical section 101 to continue to expand and deploy to its predetermined deployed shape. Because central portions of the alternating helical section are over-wrapped, rotation of catheter body 102 is not required for the alternating helical section to expand.

As outer sheath 104 is further retracted, the turns of alternating helical section 101 unwind and engage and conform to an inner wall of vessel V in a controlled manner. Helical portion 116b expands as outer sheath 104 is moved proximal of the distal end of alternating helical section 101. Helical portion 116b is not able to expand until the distal end of outer sheath 104 is moved proximal of apex 103b because alternating helical section 101 is wound so that apex 103b is located radially outward (i.e., outer-wrapped) and overlaps the adjacent helical portions. After the distal end of outer sheath 104 is moved proximal of apex 103b, helical portions 114b and 116a are allowed to expand. Finally, after sheath 104 is moved proximal of the proximal end of alternating helical section 101, helical portion 114a is able to expand, as illustrated in FIG. 15C.

Proximal movement of outer sheath 104 may be halted once the distal edge of outer sheath 104 is substantially aligned with proximal stop 112 to allow alternating helical section 101 to expand. It will be appreciated that because of the sequence of deployment of alternating helical section 101, the location of the deployed alternating helical section 101 may be easily controlled and the problems encountered in previous systems (e.g., stent jumping) may be avoided.

Figure 15D:
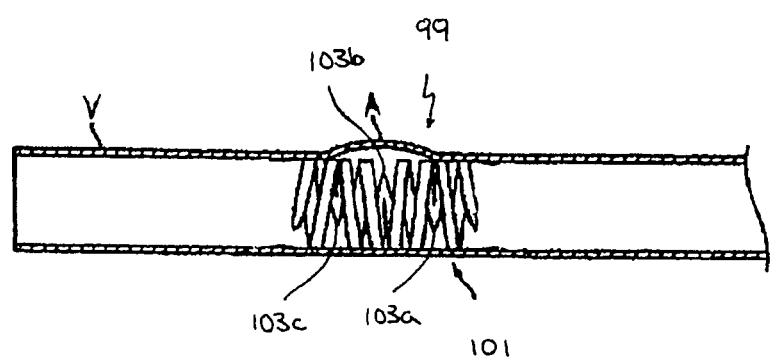

When vascular prosthesis 109 is fully deployed, delivery system 100 is proximally retracted over guidewire 108 and withdrawn from the patient's vessel, and guidewire 108 is removed. After removal of delivery system 100 and guidewire 108, vascular prosthesis 109 remains deployed, as shown in FIG. 15D.

In the present-invention, the partial overlap of portions of alternating helical section 101 reduce the surface area that is available to frictionally engage an inner surface of outer sheath 104. Furthermore, the sequence of deployment of the alternating helices included in alternating helical section 101 also assures that the prosthesis remains properly located during deployment. Advantageously, the helical portions of the alternating helical section will be accurately deployed within vessel V, with substantially no proximal or distal shifting or foreshortening of the prosthesis with respect to the vessel as the outer sheath of the delivery device is retracted.

A further advantage over the above-mentioned publications is that the configuration of the alternating helical section provides dampening characteristics for longitudinal, torsional and buckling forces applied to the vascular prosthesis.

Although a method of treating diseased vessels has been described, it will be apparent from the method described herein that the vascular prosthesis may be used in a variety of procedures. For example, vascular prosthesis also may be used in general stenting procedures, for example, to maintain patency in a vessel after a carotid angioplasty procedure, or may be used to exclude or reduce flow to an aneurysm, or may be used as an intravascular drug delivery device, or may be used in other applications apparent to those skilled in the art.

In accordance with another aspect of the present invention, the vascular prosthesis of the present invention is configured to be flexible enough to substantially conform to the shape of vessel V without causing the vessel to remodel. In particular, the alternating direction of rotation of the helical portions of the alternating helical section allow for increased flexibility of the prosthesis. In addition, the use of different lengths and pitches of the helical portions is used to provide desired flexibility. It will be appreciated that selecting different lengths and/or pitches of the helical portions may be used to create a vascular prosthesis that has portions that are more flexible than others or to provide different sized gaps between turns of a helical portion, such as, for example, to allow flow into side branches.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A vascular prosthesis for implantation in a body vessel having a vessel wall, the vascular prosthesis comprising:
an alternating helical section placeable in a contracted state, suitable for transluminal insertion into the body vessel, and in an expanded state,
the alternating helical section having a flat ribbon-like helical structure with a width and thickness, the width being substantially greater than the thickness,
the alternating helical section comprising first, second and third helical portions, the helical portions arranged in series with each helical portion having proximal and distal ends, wherein the first and the third helical portions have a direction of rotation about a longitudinal axis of the prosthesis opposite to that of the second helical portion,
the distal end of the first helical portion connected directly to the proximal end of the second helical portion at a first apex, the distal end of the second helical portion connected directly to the proximal end of the third helical portion at a second apex, the first helical portion being connected to the second helical portion only at the first apex,
the distal ends of the first and second helical portions and the proximal ends of the second and third helical portions having converging sides, each of the first and second apices also comprising converging sides terminating at a narrowed tip, and
the entire first and second helical portions have different lengths to place the first and second apices at substantially different circumferential positions when in the expanded state, whereby a mechanical characteristic of the vascular prosthesis can be affected by said different positions.

2. The vascular prosthesis of claim 1, wherein the alternating helical section includes an even number of helical portions having a first direction of rotation and an odd number of helical portions having a second direction of rotation, wherein the connected helical portions define an even number of apices.

3. The vascular prosthesis of claim 1, wherein the first and second helical portions have different pitches.

4. The vascular prosthesis of claim 1, wherein the alternating helical section comprises a free end configured to be located radially outward of the adjacent helical portion when the vascular prosthesis is in the contracted state.

5. The vascular prosthesis of claim 1, wherein the alternating helical section comprises a free end configured to be located radially inward of the adjacent helical portion when the vascular prosthesis is in the contracted state.

6. The vascular prosthesis of claim 1, wherein at least one helical portion is a helical mesh.

7. The vascular prosthesis of claim 1, further comprising a therapeutic agent disposed on a surface of the alternating helical section.

8. The vascular prosthesis of claim 1, further comprising a polymer disposed on a surface of the alternating helical section.

9. The vascular prosthesis of claim 8, wherein the polymer is disposed on a surface of the alternating helical section and configured to be a stent graft.

10. The vascular prosthesis of claim 8, wherein the polymer is configured to elute a therapeutic agent.

11. The vascular prosthesis of claim 1, further comprising a radially expanding anchor section joined to a first end of the alternating helical section.

12. The vascular prosthesis of claim 11, wherein the alternating helical section and the first anchor section each are capable of assuming a contracted state suitable for transluminal insertion into the body vessel and a deployed state wherein the helical section and first anchor section are configured to engage the vessel wall.

13. The vascular prosthesis of claim 1, wherein the alternating helical section comprises a shape memory material.

14. The vascular prosthesis of claim 13, wherein the shape memory material is a nickel titanium alloy.

15. The vascular prosthesis of claim 11, wherein the alternating helical section and the anchor section are separately formed and then coupled together.

16. The vascular prosthesis of claim 11, wherein the alternating helical section and the anchor section are integrally formed.

17. The vascular prosthesis of claim 1, wherein the mechanical characteristic that can be affected by said different positions comprises at least one of flexibility, gap control, and compression resistance.

18. A vascular prosthesis for implantation in a body vessel having a vessel wall, the vascular prosthesis comprising:

an alternating helical section placeable in a contracted state, suitable for transluminal insertion into the body vessel, and in an expanded state, the alternating helical section having a flat ribbon-like helical structure with a width and thickness, the width being substantially greater than the thickness, the alternating helical section comprising first, second and third helical portions, the helical portions arranged in series with each helical portion having proximal and distal ends, wherein the first and the third helical portions have a direction of rotation about a longitudinal axis of the prosthesis opposite to that of the second helical portion, the distal end of the first helical portion connected directly to the proximal end of the second helical portion at a first apex, the distal end of the second helical portion connected directly to the proximal end of the third helical portion at a second apex, the first helical portion being connected to the second helical portion only at the first apex, the distal ends of the first and second helical portions and the proximal ends of the second and third helical portions having converging sides, each of the first and second apices also comprising converging sides terminating at a narrowed tip, and means for placing the first and second apices at substantially different circumferential positions when in the expanded state, whereby a mechanical characteristic of the vascular prosthesis can be affected by said different positions, the mechanical characteristic comprising at least one of flexibility, gap control, and compression resistance.

\* \* \* \* \*